United States Patent
Iaccino et al.

(10) Patent No.: US 8,138,384 B2
(45) Date of Patent: Mar. 20, 2012

(54) PRODUCTION OF ALKYLATED AROMATIC HYDROCARBONS FROM METHANE

(75) Inventors: Larry L. Iaccino, Seabrook, TX (US); Elizabeth L. Stavens, Seabrook, TX (US); Gary D. Mohr, Houston, TX (US); Matthew J. Vincent, Baytown, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1190 days.

(21) Appl. No.: 11/792,324

(22) PCT Filed: Dec. 2, 2005

(86) PCT No.: PCT/US2005/043523
§ 371 (c)(1),
(2), (4) Date: Jun. 5, 2007

(87) PCT Pub. No.: WO2006/068800
PCT Pub. Date: Jun. 29, 2006

(65) Prior Publication Data
US 2008/0058564 A1    Mar. 6, 2008

Related U.S. Application Data

(60) Provisional application No. 60/638,605, filed on Dec. 22, 2004.

(51) Int. Cl.
*C07C 15/00* (2006.01)

(52) U.S. Cl. ........ 585/415; 585/407; 585/418; 585/424; 585/446; 585/448; 585/470; 585/943

(58) Field of Classification Search .................. None
See application file for complete search history.

(56) References Cited

U.S. PATENT DOCUMENTS

| | | | |
|---|---|---|---|
| 4,727,206 | A | 2/1988 | Clayson et al. |
| 5,026,937 | A | 6/1991 | Bricker |
| 5,336,825 | A | 8/1994 | Choudhary et al. |
| 5,348,982 | A | 9/1994 | Herbolzheimer et al. |
| 5,491,270 | A | 2/1996 | Chin et al. |
| 5,936,135 | A | 8/1999 | Choudhary et al. |
| 6,114,279 | A | 9/2000 | Fukui et al. |

(Continued)

FOREIGN PATENT DOCUMENTS

EP    1018563 A1 *  7/2000

(Continued)

OTHER PUBLICATIONS

Ma et al., "On the Induction Period of Methane Aromatization over Mo-Based Catalysts", Journal of Catalysis, 194, (2000), pp. 105-114.

(Continued)

*Primary Examiner* — Tam M Nguyen
(74) *Attorney, Agent, or Firm* — Andrew B. Griffis

(57) ABSTRACT

In a process for converting methane to alkylated aromatic hydrocarbons, a feed containing methane is contacted with a dehydrocyclization catalyst under conditions effective to convert said methane to aromatic hydrocarbons and produce a first effluent stream comprising aromatic hydrocarbons and hydrogen. At least a portion of said aromatic hydrocarbon from said first effluent stream is then contacted with an alkylating agent under conditions effective to alkylate said aromatic hydrocarbon and produce an alkylated aromatic hydrocarbon having more alkyl side chains than said aromatic hydrocarbon prior to the alkylating.

2 Claims, 3 Drawing Sheets

U.S. PATENT DOCUMENTS

| | | | |
|---|---|---|---|
| 6,239,057 B1 | 5/2001 | Ichikawa et al. |
| 6,426,442 B1 | 7/2002 | Ichikawa et al. |
| 6,552,243 B2 | 4/2003 | Allison et al. |
| 2002/0035305 A1 | 3/2002 | Ichikawa et al. |
| 2002/0112989 A1 | 8/2002 | Shih et al. |
| 2003/0144565 A1 | 7/2003 | Allison et al. |
| 2004/0015025 A1 | 1/2004 | Bellussi et al. |
| 2004/0097770 A1 | 5/2004 | Dakka et al. |

FOREIGN PATENT DOCUMENTS

| | | |
|---|---|---|
| RU | 2 135 441 | 8/1999 |

OTHER PUBLICATIONS

Liu et al., "Non-oxidative Dehydroaromatization of Methane over Ga-promoted Mo-HZSM-5-based Catalysts", Applied Catalysis A: General, 214, (2001), pp. 95-102.

Japan Chemical Week Incorporating Asia Report, "Benzene Synthesized Directly from Methane: Mitsubishi Chem", The Chemical Daily Co., Ltd., vol. 46, No. 2337, ISSN 0047-1755, Oct. 6, 2005.

* cited by examiner

PRODUCTION OF ALKYLATED AROMATIC HYDROCARBONS FROM METHANE

CROSS REFERENCE TO RELATED APPLICATIONS

This application is a National Stage Application of International Application No. PCT/US2005/043523 filed Dec. 2, 2005, which claims the benefit of Provisional Application No. 60/638,605, filed Dec. 22, 2004, the entirety of which is incorporated by reference.

FIELD

This application describes a process for producing aromatic hydrocarbons from methane and, in particular, from natural gas.

BACKGROUND

Aromatic hydrocarbons, particularly benzene, toluene, ethylbenzene and xylenes, are important commodity chemicals in the petrochemical industry. Currently, aromatics are mostly frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is a particularly attractive method of upgrading natural gas, providing the attendant technical difficulties can be overcome.

A large majority of the processes for converting methane to liquid hydrocarbons involve first conversion of the methane to synthesis gas, a blend of $H_2$ and CO. Production of synthesis gas is capital and energy intensive; therefore routes that do not require synthesis gas generation are preferred.

A number alternative processes have been proposed for converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

Dehydroaromatization of methane via high-temperature reductive coupling has also been proposed as a route for upgrading methane into higher hydrocarbons, particularly ethylene, benzene and naphthalene. Thus, for example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

U.S. Pat. No. 5,026,937 discloses a process for the aromatization of methane which comprises the steps of passing a feed stream, which comprises over 0.5 mole percent hydrogen and 50 mole percent methane, into a reaction zone having at least one bed of solid catalyst comprising ZSM-5 and phosphorous-containing alumina at conversion conditions which include a temperature of 550° C. to 750° C., a pressure less than 10 atmospheres absolute (1000 kPaa) and a gas hourly space velocity of 400 to 7,500 $hr^{-1}$. The product effluent is said to include methane, hydrogen, at least 3 mole % $C_2$ hydrocarbons and at least 5 mole % $C_6$-$C_8$ aromatic hydrocarbons. After condensation to remove the $C_4$+ fraction, cryogenic techniques are proposed to separate the hydrogen and light hydrocarbons (methane, ethane, ethylene, etc.) in the product effluent.

U.S. Pat. No. 5,936,135 discloses a low temperature, non-oxidative process for the conversion of a lower alkane, such as methane or ethane, to aromatic hydrocarbons. In this process, the lower alkane is mixed with a higher olefin or paraffin, such as propylene or butene, and the mixture is contacted with a pretreated bifunctional pentasil zeolite catalyst, such as GaZSM-5, at a temperature of 300° C. to 600° C., a gas hourly space velocity of 1000 to 100000 $cm^3g^{-1}hr^{-1}$ and a pressure of 1 to 5 atmosphere (100 to 500 kPa). Pretreatment of the catalyst involves contacting the catalyst with a mixture of hydrogen and steam at a temperature 400° C. to 800° C., a pressure of 1 to- 5 atmosphere (100 to 500 kPa) and a gas hourly space velocity of at least 500 $cm^3g^{-1}hr^{-1}$ for a period of at least 0.5 hour and then contacting the catalyst with air or oxygen at a temperature of 400° C. to 800° C., a gas hourly space velocity of at least 200 $cm^3g^{-1}hr^{-1}$ and a pressure of 1 to 5 atmosphere (100 to 500 kPa) for a period of at least 0.2 hour.

U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadiun, manganese, molybdenum, tungsten or a mixture thereof. The addition of CO or $CO_2$ to the feed is said to increase the yield of benzene and the stability of the catalyst.

U.S. Pat. No. 6,552,243 discloses a process for the non-oxidative aromatization of methane, in which a catalyst composition comprising a metal-loaded, crystalline aluminosilicate molecular sieve is initially activated by treatment with a mixture of hydrogen and a $C_2$ to $C_4$ alkane, preferably butane, and then the activated catalyst is contacted with a feed stream comprising at least 40 mole percent methane at a temperature of 600° C. to 800° C., a pressure of less than 5 atmosphere absolute (500 kPaa), and a weight hourly space velocity (WHSV) of 0.1 to 10 $hr^{-1}$.

Russian Patent No. 2,135,441 discloses a process for converting methane to heavier hydrocarbons, in which the methane is mixed with at least 5 wt % of a $C_3$+ hydrocarbon, such as benzene, and then contacted in a multi-stage reactor system with a catalyst comprising metallic platinum having a degree of oxidation greater than zero at a methane partial pressure of at least 0.05 MPa and a temperature of at least 440° C. Hydrogen generated in the process may be contacted with oxides of carbon to generate additional methane that, after removal of the co-produced water, can be added to the methane feed. The products of the methane conversion are a $C_2$-$C_4$ gaseous phase and a $C_5$+ liquid phase but, according the Examples, there is little (less than 5 wt %) or no net increase in aromatic rings as compared with the feed.

Existing proposals for the conversion of methane to aromatic hydrocarbons suffer from a variety of problems that have limited their commercial potential. Thus the major aromatic products of most methane conversion processes are benzene and naphthalene. While benzene has potential value as a chemical feedstock it has a limited chemical market and is not viable as a fuel source due to health and environmental issues. Naphthalene has an even more limited chemicals market and is more challenging for use as a fuel due to health and environmental issues plus a melting point higher than ambient temperature. In contrast, alkylaromatic compounds, such as toluene, ethylbenzene, xylenes and dimethyl naphthalenes, generally have higher utility as intermediates in the petrochemical industry.

In addition, oxidative coupling methods generally involve highly exothermic and potentially hazardous methane combustion reactions, frequently require expensive oxygen generation facilities and produce large quantities of environmentally sensitive carbon oxides. On the other hand, existing reductive coupling techniques frequently have low selectivity to aromatics and may require expensive co-feeds to improve conversion and/or aromatics selectivity. Moreover, any reductive coupling process generates large quantities of hydrogen and so, for economic viability, requires a route for effective utilization of the hydrogen by-product. Since natural gas fields are frequently at remote locations, effective hydrogen utilization can present a substantial challenge.

A particular difficulty in using natural gas as a methane source concerns the fact that many natural gas fields around the world contain large quantities, sometimes in excess of 50%, of carbon dioxide. Not only is carbon dioxide a target of increasing governmental regulation because of its potential contribution to global climate change, but also any process which requires separation and disposal of large quantities of carbon dioxide from natural gas is likely to be economically prohibitive. In fact, some natural gas fields have such high carbon dioxide levels as to be currently considered economically unrecoverable.

There is therefore a need for an improved process for converting methane, particularly methane from natural gas streams, to aromatic hydrocarbons, particularly alkylated aromatic hydrocarbons.

SUMMARY

In one aspect, this application describes a process for converting methane to alkylated aromatic hydrocarbons, the process comprising:

(a) contacting a feed containing methane with a dehydrocyclization catalyst under conditions effective to convert said methane to aromatic hydrocarbons and produce a first effluent stream comprising aromatic hydrocarbons and hydrogen; and (b) contacting at least a portion of said aromatic hydrocarbon from said first effluent stream with an alkylating agent under conditions effective to alkylate said aromatic hydrocarbon and produce an alkylated aromatic hydrocarbon having more alkyl side chains than said aromatic hydrocarbon prior to the alkylating.

Conveniently, said feed in (a) also contains at least one of $H_2$, $H_2O$, CO and $CO_2$.

Conveniently, said feed in (a) contains less than 5 wt % of $C_3$+ hydrocarbons. As used herein, the term "$C_3$+ hydrocarbons" means hydrocarbons having 4 or more carbon atoms.

Conveniently, said conditions in (a) are non-oxidizing conditions By "non-oxidizing" is meant that oxidizing agents (such as, $O_2$, $NO_x$ and metal oxides which can release oxygen to oxidize methane to $CO_x$) are present at less than 5%, preferably at less then 1%, most preferably at less than 0.1%, of the amount required for stoichiometric oxidation of the methane.

Typically said conditions in (a) include a temperature of 400° C. to 1200° C., such as 500° C. to 975° C., for example 600° C. to 950° C.

Conveniently, the process also comprises recovering said at least a portion of said aromatic hydrocarbon, typically benzene and/or naphthalene, from said first effluent stream before said contacting (b).

In one embodiment, the alkylating agent used in said contacting (b) comprises ethylene produced in said contacting (a).

In another embodiment, the alkylating agent used in said contacting (b) comprises carbon monoxide and hydrogen or a reaction product thereof.

In one embodiment, the process further comprises reacting at least part of the hydrogen from said first effluent stream with an oxygen-containing species to produce a second effluent stream having a reduced hydrogen content compared with said first effluent stream.

Conveniently, said oxygen-containing species comprises an oxide of carbon, such as carbon dioxide, for example carbon dioxide from a natural gas stream which may also contain at least part of the methane in the feed in (a). In one embodiment, the reacting with an oxygen-containing species produces water and methane, ethane or a mixture of methane and ethane and the process additionally comprises removing water from said second effluent stream and feeding at least part of the methane and/or ethane from the second effluent stream to said contacting (a). In another embodiment, the reacting with an oxygen-containing species produces one or more of $C_2$ to $C_5$ paraffins and olefins, single-ring aromatic hydrocarbons and $C_1$ to $C_3$ alcohols.

In a further aspect, this application describes a process for converting methane to alkylated aromatic hydrocarbons, the process comprising:

(a) contacting a feed containing methane with a dehydrocyclization catalyst under conditions effective to convert said methane to aromatic hydrocarbons and produce a first effluent stream comprising aromatic hydrocarbons and hydrogen; and (b) contacting at least a portion of said aromatic hydrocarbon from said first effluent stream with an alkylating agent under conditions effective to alkylate said aromatic hydrocarbon and produce an alkylated aromatic hydrocarbon having more alkyl side chains than said aromatic hydrocarbon prior to the alkylating;

(c) recovering said alkylated aromatic hydrocarbon; and (d) reacting at least part of the hydrogen from said first effluent stream with an oxygen-containing species to produce a second effluent stream having a reduced hydrogen content compared with said first effluent stream.

In yet a further aspect, this application describes a process for converting methane to alkylated aromatic hydrocarbons, the process comprising:

(a) contacting a feed containing methane with a dehydrocyclization catalyst under conditions effective to convert said methane to aromatic hydrocarbons and produce a first effluent stream comprising aromatic hydrocarbons and hydrogen;

(b) contacting at least a portion of said aromatic hydrocarbon in said first effluent stream with an alkylating agent under conditions effective to alkylate said aromatic hydrocarbon and produce an alkylated aromatic hydrocarbon having more alkyl side chains than said aromatic hydrocarbon prior to the alkylating;

(c) recovering said alkylated aromatic hydrocarbon;

(d) reacting at least part of the hydrogen from said first effluent stream with CO and/or $CO_2$ to produce a second effluent stream comprising water and hydrocarbon; and (e) separating at least a portion of said water from said second effluent stream to produce a third effluent stream comprising hydrocarbon; and (f) recycling at least part of the hydrocarbon in said third effluent stream to said contacting (a).

DETAILED DESCRIPTION OF THE EMBODIMENTS

Figure 1:
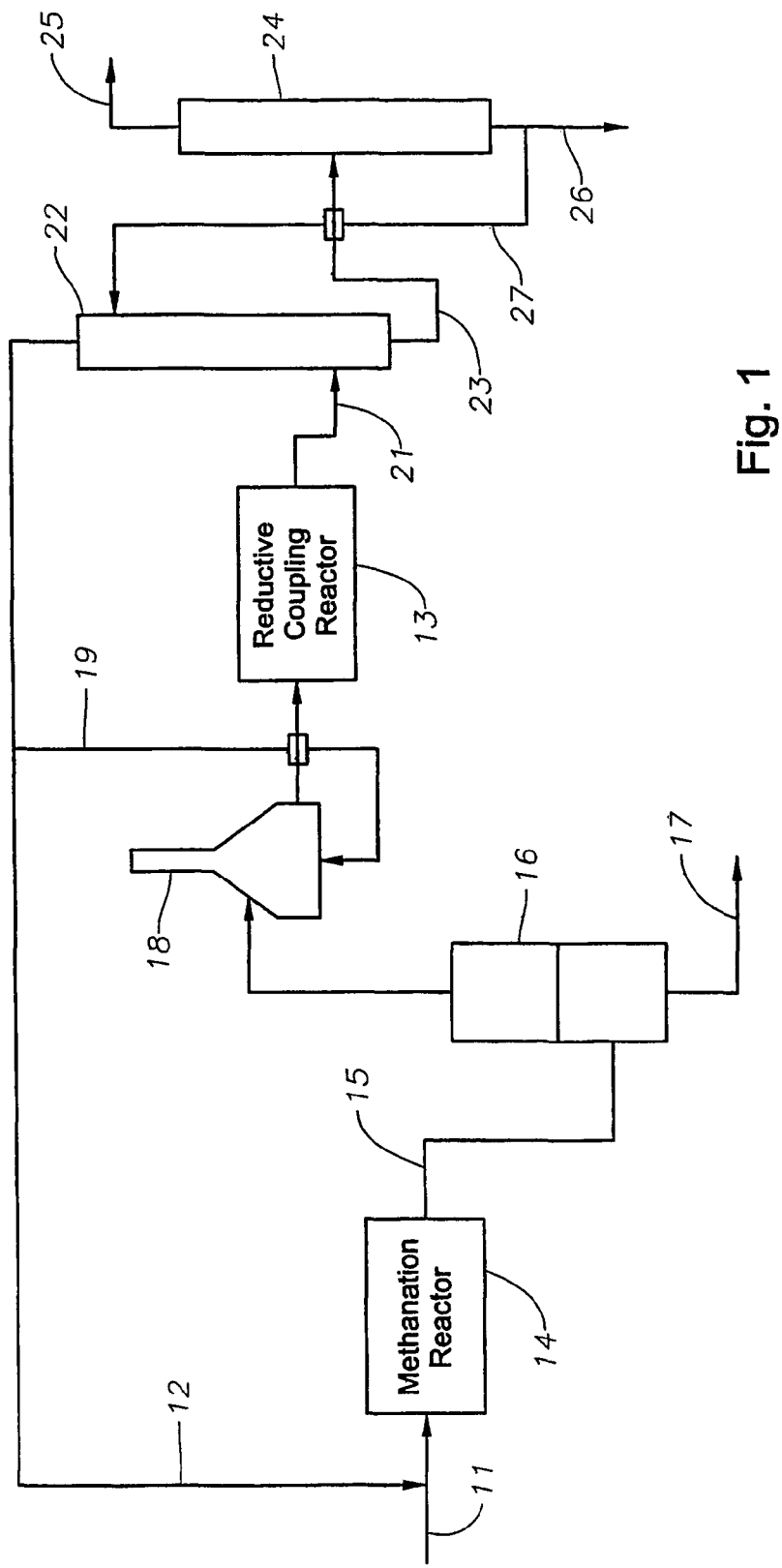
FIG. 1 is a flow diagram of a process for converting methane to aromatic hydrocarbons according to a first example of the invention.

This application describes a process for converting methane to alkylated aromatic hydrocarbons. The process involves initially subjecting a feed containing methane, typically together with $H_2$, CO and/or $CO_2$, to a dehydrocyclization step under conditions effective to convert methane to aromatic hydrocarbons and produce a first effluent stream comprising aromatic hydrocarbons, particularly benzene and naphthalene, and hydrogen. With or without an initial recovering step, at least a portion of said aromatic hydrocarbon in the first effluent stream is then contacted with an alkylating agent under conditions effective to alkylate the aromatic hydrocarbon and produce alkylated aromatic hydrocarbon having more alkyl side chains than said initially produced aromatic hydrocarbon.

In a further embodiment, the alkylated aromatic hydrocarbon is then recovered, and the remainder of the first effluent stream may be subjected to a hydrogen rejection step in which at least part of the hydrogen from said first effluent stream is reacted with an oxygen-containing species to produce a second effluent stream having a reduced hydrogen content compared with the first effluent stream. Typically the hydrogen rejection step produces additional hydrocarbon species, such as methane, which are recycled to the dehydrocyclization step.

Feedstock

Any methane-containing feedstock can be used in the process of the invention but in general the present process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can of course be converted to desired aromatics products in the dehydrocyclization step. In addition, as will be discussed below, carbon dioxide can be utilized in the production of aromatics either directly in the dehydrocyclization step or indirectly through conversion to methane and/or ethane in the hydrogen rejection step.

Nitrogen and/or sulfur impurities are also typically present in methane-containing streams and may be removed, or reduced to low levels, prior to use of the streams in the process of the invention. In an embodiment of the invention, the feed to the dehydrocyclization step contains less than 100 ppm, for example less than 10 ppm, such as less than 1 ppm each of nitrogen and sulfur compounds.

In addition to methane, the feed to the dehydrocyclization step may contain at least one of hydrogen, water, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include, but are not limited to, flue gases, LNG plants, hydrogen plants, ammonia plants, glycol plants and phthalic anhydride plants.

In one embodiment, the feed to the dehydrocyclization step contains carbon dioxide and comprises 90 to 99.9 mol %, such as 97 to 99 mol %, methane and 0.1 to 10 mol %, such as 1 to 3 mol %, $CO_2$. In another embodiment, the feed to the dehydrocyclization step contains carbon monoxide and comprises 80 to 99.9 mol %, such as 94 to 99 mol %, methane and 0.1 to 20 mol %, such as 1 to 6 mol %, CO. In a further embodiment, the feed to the dehydrocyclization step contains steam and comprises 90 to 99.9 mol %, such as 97 to 99 mol %, methane and 0.1 to 10 mol %, such as 1 to 5 mol %, steam. In yet a further embodiment, the feed to the dehydrocyclization step contains hydrogen and comprises 80 to 99.9 mol %, such as 95 to 99 mol %, methane and 0.1 to 20 mol %, such as 1 to 5 mol %, hydrogen.

The feed to the dehydrocyclization step can also contain higher hydrocarbons than methane, including aromatic hydrocarbons. Such higher hydrocarbons can be recycled from the hydrogen rejection step, added as separate co-feeds or can be present in the methane stream, such as, for example, when ethane is present in a natural gas feed. Higher hydrocarbons recycled from the hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3+$ hydrocarbons.

Dehydrocyclization

In the dehydrocyclization step of the present process, the methane containing feed is contacted with a dehydrocyclization catalyst under conditions, normally non-oxidizing conditions and preferably reducing conditions, effective to convert the methane to higher hydrocarbons, including benzene and naphthalene. The principal reactions involved are as follows:

  (Reaction 1)

  (Reaction 2)

  (Reaction 3)

Carbon monoxide and/or dioxide that may be present in the feed improves catalyst activity and stability by facilitating reactions such as:

  (Reaction 4)

but negatively impacts equilibrium by allowing competing reactions, such as;

  (Reaction 5).

Any dehydrocyclization catalyst effective to convert methane to aromatics can be used in the process of the invention, although generally the catalyst will include a metal component, particularly a transition metal or compound thereof, on an inorganic support. Conveniently, the metal component is present in an amount between 0.1% and 20%, such as between 1% and 10%, by weight of the total catalyst.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, germanium, silicon, indium, tin, lead, bismuth and transuranium metals. Such metal components may be present in elemental form or as metal compounds, such as oxides, carbides, nitrides and/or phosphides, and may be employed alone or in combination. Platinum and osmium can also be used as one of the metal component but, in general, are not preferred.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50 and SBA-15.

Examples of preferred catalysts include molybdenum, tungsten, rhenium and compounds and combinations thereof on ZSM-5, silica or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

The dehydrocyclization step can be conducted over a wide range of conditions including a temperature of 400° C. to 1200° C., such as 500° C. to 975° C., for example 600° C. to 950° C., a pressure of 1 kPa to 1000 kPa, such as 10 to 500 kPa, for example 50 kPa to 200 kPa and a weight hourly space velocity of 0.01 to 1000 $hr^{-1}$, such as 0.1 to 500 $hr^{-1}$, for example 1 to 20 $hr^{-1}$. Conveniently, the dehydrocyclization step is conducted in the absence of $O_2$.

The dehydrocyclization step can be conducted in one or more fixed beds, moving beds or fluidized bed reactors, with catalyst regeneration being conducted in-situ or ex-situ with air, oxygen, carbon dioxide, carbon monoxide, water or hydrogen.

The dehydrocyclization reaction is endothermic and, hence where the reaction is conducted in a plurality of stages, it may be necessary to employ interstage heating to return the feed to the required reaction temperature. The fuel required to provide the interstage heating may conveniently obtained by removing and combusting a sidestream from the dehydrocyclization effluent, after separation of the aromatic components and/or after separation of the alkylated aromatic components. In addition, where the reaction occurs in the presence of a moving bed of catalyst, a portion or all of the heat may be supplied by withdrawing a portion of the catalyst from the bed, heating the catalyst by, for example, combustion of coke on the catalyst, and then returning the heated catalyst to the moving catalyst bed.

The major components of the effluent from the dehydrocyclization step are hydrogen, benzene, naphthalene, carbon monoxide, ethylene, coke and unreacted methane. Typically, the effluent contains at least 5 wt %, such as at least 10 wt %, for example at least 20 wt %, preferably at least 30 wt %, more aromatic rings than the feed. It is to be appreciated that references herein to the first effluent stream comprising at least 5 wt % more aromatic rings than the feed is intended to mean that the total number of aromatic rings in the first effluent stream should exceed the total number of aromatic rings in the feed by at least 5 wt %. Changes in substituents on any aromatic rings between the feed and the first effluent stream are not included in this calculation.

The benzene and naphthalene are then subjected to an alkylation step to produce higher value materials, such as xylenes and dimethyl naphthalenes. This is conveniently achieved without prior separation of the benzene and naphthalene from the dehydrocyclization effluent. However, if desired, the benzene and naphthalene can be separated from the dehydrocyclization effluent, for example, by solvent extraction followed by fractionation before undergoing alkylation.

Aromatics Alkylation

The alkylation process of the invention involves contacting part or all of the aromatic hydrocarbons in the dehydrocyclization effluent with an alkylating agent, such as an olefin, alcohol or alkyl halide, in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e., those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

Alkylation with Olefins

In one embodiment of the present process, benzene is recovered from the dehydrocyclization effluent and then alkylated with an olefin, such as ethylene or propylene. The olefin may be produced as a by-product of dehydrocyclization reaction or may be produced through thermal or catalytic cracking of hydrocarbons as is well known to those skilled in the art. A means of producing higher levels of olefins in conjunction with the dehydrocyclization step is to inject C2+ hydrocarbons into the hot effluent of the dehydrocyclization reactor. Steam may be co-injected with the C2+ hydrocarbon to reduce coke formation. Olefins useful for alkylation can also be produced from dimethylether, methanol or higher alcohols.

Typical conditions for carrying out the vapor phase alkylation of benzene with ethylene include a temperature of from 650 to 900° F. (343 to 482° C.), a pressure of atmospheric to 3000 psig (100 to 20,800 kPa), a WHSV based on ethylene of from 0.5 to 4.0 hr$^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from 0.1 to 20 hr$^{-1}$ and a mole ratio of benzene to ethylene of from 1:1 to 30:1. Typical conditions for carrying out the liquid phase alkylation of benzene with propylene include a temperature of from about 176 to 392° F. (80 to 200° C.), a pressure of atmospheric to 3000 psig (100 to 20,800 kPa), a WHSV based on propylene of from 0.5 to 4.0 hr$^{-1}$ and a mole ratio of benzene to propylene of from 1:1 to 30:1

Preferably, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5, MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM48, which has been modified by steaming so as to have a Diffusion Parameter for 2,2dimethylbutane of 0.1-15 sec$^{-1}$ when measured at a temperature of 120° C. and a 2,2dimethylbutane pressure of 60 torr (8 kPa). Such a process is selective to the production of para-xylene and is described in, for example, U.S. Pat. No. 6,504,272, incorporated herein by reference. Where the methanol or DME is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847; 5,001,295; 6,011,190 and 6,018,086, incorporated herein by reference.

Toluene/Benzene Methylation to Produce Xylenes

Typical single ring aromatic product from the dehydrocyclization reaction is predominately benzene with a reduced level of toluene. To increase the total yield of xylenes, both the product from the dehydrocyclization reactor and recycled benzene and toluene separated from the xylene product by distillation can be methylated.

In many instances it will be desirable to produce xylenes while minimizing the amount of ethylbenzene; in those instances, ethylene which may be present in the feed to the alkylation zone should be hydrogenated to ethane so as to prevent it from alkylating the benzene or toluene. If both xylenes and ethylbenzene are desired products, ethylbenzene synthesis and recovery may be performed prior to the xylene synthesis step for ease of separation or may be conducted in the same reactor to produce a mixed product.

The methylation reaction is preferably carried out in the vapor phase, with typical reaction conditions including a temperature from 300° C. to 700° C., preferably 400° C. to 700° C., a pressure from 1 to 1000 psig (100 to 7000 kPa), and a weight hourly space velocity of between 0.1 and 200 hr$^{-1}$, preferably between 1 and 100 hr$^{-1}$. The molar ratio of toluene and benzene to methylating agent can vary and will usually be from 0.1:1 to 20:1, preferably from 2:1 to 4:1. Hydrogen gas and/or steam can be supplied to the reaction as an anticoking agent and diluent. The methylating agent is usually supplied to the methylation reaction zone through multiple feed points, e.g., 3-6 feed points. The reaction may be carried out in a bed of stationary catalyst, a moving bed reactor, or a fluidized bed reactor. Due to the exotherm of the reaction, heat removal or addition or low temperature quench may be required.

Typical methylating agents include methanol, dimethylether, methylchloride, methylbromide, methylcarbonate, acetaldehyde, dimethoxyethane, acetone, and dimethylsulfide, with methanol and dimethylether being preferred. The methylating agent can also be formed from synthesis gas, e.g., the agent can be formed from the $H_2$, CO, and/or $CO_2$ of synthesis gas. The methylating agent can be formed from the synthesis gas within the methylation reaction zone.

Catalysts suitable for use in the methylation reaction include naturally occurring and synthetic crystalline molecular sieves. Examples of such molecular sieves include large pore molecular sieves, intermediate size pore molecular sieves, and small pore molecular sieves. These molecular sieves are described in "Atlas of Zeolite Framework Types", eds. Ch. Baerlocher, W. H. Meier, and D. H. Olson, Elsevier, Fifth Edition, 2001, which is hereby incorporated by reference. A large pore molecular sieve generally has a pore size of at least about 7 Å and includes IWW, LTL, VFI, MAZ, MEI, FAU, EMT, OFF, *BEA, and MOR framework type molecular sieves (IUPAC Commission of Zeolite Nomenclature). Examples of suitable large pore molecular sieves, include ITQ-22, mazzite, offretite, zeolite L, VPI-5, zeolite Y, zeolite X, omega, Beta, ZSM-3, ZSM-4, ZSM-18, ZSM-20, SAPO-37, and MCM-22. An intermediate pore size molecular sieve generally has a pore size from about 5 Å to about 7 Å and includes, for example, ITH, ITW, MFI, MEL, MTW, EUO, MTT, HEU, FER, MFS, and TON framework type molecular sieves. Examples of suitable intermediate pore size molecular sieves, include ITQ-12, ITQ-13, ZSM-5, ZSM-12, ZSM-22, ZSM-23, ZSM-34, ZSM-35, ZSM-38, ZSM-48, ZSM-50, ZSM-57, silicalite, and silicalite 2. A small pore size molecular sieve has a pore size from about 3 Å to about 5 Å and includes, for example, CHA, ERI, KFI, LEV, and LTA framework type molecular sieves. Examples of suitable small pore molecular sieves include ZK-4, SAPO-34, SAPO-35, ZK-14, SAPO-42, ZK-21, ZK-22, ZK-5, ZK-20, zeolite A, erionite, chabazite, zeolite T, gmelinite, and clinoptilolite.

Other molecular sieve catalysts particularly suited for the methylation reaction are zeolite bound zeolite catalysts. These catalysts, as well as their method of preparation, are described in U.S. Pat. No. 5,994,603, which is hereby incorporated by reference. The zeolite bound zeolite catalysts will comprise first crystals of an acidic intermediate pore size first molecular sieve and a binder comprising second crystals of a second molecular sieve. Preferably, the zeolite bound zeolite catalyst contains less than 10 percent by weight based on the total weight of the first and second zeolite of non-zeolitic binder, e.g., amorphous binder. An example of such a catalyst comprises first crystals of a MFI or MEL structure type, e.g., ZSM-5 or ZSM-11, and a binder comprising second crystals of MFI or MEL structure type, e.g., Silicalite 1 or Silicalite 2.

Typically, the molecular sieve used in the methylation process will have an alpha value of less than 100, more preferably less than 50, even more preferably less than 25, and most preferably less than 10. As used herein, the alpha value is a measurement of the Bronsted acid activity of the selectivated molecular sieve, i.e. it discounts the effects of the addition of the hydrogenation component on the alpha value of the molecular sieve. The alpha test is described in U.S. Pat. No. 3,354,078 and in the Journal of Catalysis, Vol. 4, 522-529 (1965); Vol. 6, 278 (1966); and Vol. 61, 395 (1980), each incorporated herein by referenced. The experimental conditions of the alpha test preferably include a constant temperature of 538° C. and a variable flow rate as described in detail in the Journal of Catalysis, Vol. 61, 395 (1980). Typically, molecular sieves having a higher silica to alumina ratio will have a. lower alpha value. Regardless, the alpha activity of a catalyst can be reduced in accordance with techniques known to those of ordinary skill in the art. For example, the alpha activity of a catalyst may be reduced by (1) steaming the catalyst at appropriate conditions, or (2) ion exchanging the catalyst with cations such as alkali metal ions.

In one embodiment, the molecular sieve catalyst is selectivated for the production of the desired alkylated product, particularly para-xylene. The catalyst can be selectivated by treating its surface with compounds of phosphorus and/or magnesium and/or various metal oxides such as alkaline earth metal oxides, e.g., calcium oxide, magnesium oxide, etc. rare earth metal oxides, lanthanum oxide, and other metal oxides such as boron oxide, titania, antimony oxide, and manganese oxide. Preferred ranges for such treatment are from 0.1 wt. % to 25 wt. %, more preferably from 1 wt. % to 10 wt. % of such compounds based on the weight of the catalyst.

The selectivation may also be accomplished by depositing coke on the catalyst. Coke selectivation can be carried out during the methylation reaction, such as by operating the methylation reaction at conditions which allow the deposition of coke on the catalyst. Also, the catalyst can be preselectivated with coke, for example, by exposing the catalyst in the reactor to a thermally decomposable organic compound, e.g., benzene, toluene, etc. at a temperature in excess of the decomposition temperature of said compound, e.g., from 400° C. to 650° C., more preferably 425° C. to 550° C., at a WHSV in the range of from 0.1 to 20 lbs. of feed per pound of catalyst per hour, at a pressure in the range of from 1 to 100 atmospheres, and in the presence of 0 to 2 moles of hydrogen, more preferably from 0.1 to 1 moles of hydrogen per mole of organic compound, and optionally in the presence of 0 to 10 moles of nitrogen or another inert gas per mole of organic compound. This process is conducted for a period of time until a sufficient quantity of coke has deposited on the catalyst surface, generally at least about 2% by weight and more preferably from 8% to 40% by weight of coke.

A silicon compound may also be used to selectivate the catalyst. The silicon compound may comprise a polysiloxane including silicones, a siloxane, and a silane including disilanes and alkoxysilanes. As is known to those of ordinary skill in the art, multiple treatments may be employed to effect various degrees of selectivation.

Silicones that can be used to selectivate the catalyst include the following:

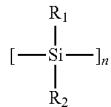

wherein $R_1$ is hydrogen, fluoride, hydroxy, alkyl, aralkyl, alkaryl or fluoro-alkyl. The hydrocarbon substituents generally contain from 1 to about 10 carbon atoms and preferably are methyl or ethyl groups. $R_2$ is selected from the same group as $R_1$, and n is an integer of at least 2 and generally in the range of 2 to 1000. The molecular weight of the silicone employed is generally between 80 to 20,000 and preferably 150 to 10,000. Representative silicones include dimethylsilicone, diethylsilicone, phenylmethylsilicone, methyl hydrogensilicone, ethylhydrogensilicone, phenylhydrogensilicone, fluoropropylsilicone, ethyltrifluoroprophysilicone, tetrachlorophenyl methyl methylethylsilicone, phenylethylsilicone, diphenylsilicone, methyltrisilicone, tetrachlorophenylethyl silicone, methylvinylsilicone and ethylvinylsilicone. The silicone need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes and polysiloxanes include as non-limiting example hexamethylcyclotrisiloxane, octamethylcyclotetrasiloxane, decamethyl cyclopentasiloxane, hexamethyldisiloxane, octamethytrisiloxane, decamethyltetrasiloxane, hexaethylcyclotrisiloxane, octaethylcyclo tetrasiloxane, hexaphenylcyclotrisiloxane and octaphenylcyclo-tetrasiloxane.

Useful silanes, disilanes, or alkoxysilanes include organic substituted silanes having the general formula:

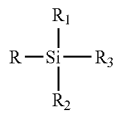

wherein R is a reactive group such as hydrogen, alkoxy, halogen, carboxy, amino, acetamnide, trialkylsilyoxy, $R_1$, $R_2$ and $R_3$ can be the same as R or can be an organic radical which may include alkyl of from 1 to 40 carbon atoms, alkyl or aryl carboxylic acid wherein the organic portion of alkyl contains 1 to 30 carbon atoms and the aryl group contains 6 to 24 carbons which may be further substituted, alkylaryl and arylalkyl groups containing 7 to 30 carbon atoms. Preferably, the alkyl group for an alkyl silane is between 1 and 4 carbon atoms in chain length. Mixtures may also be used.

The silanes or disilanes include, as non-limiting examples, dimethylphenylsilane, phenytrimethylsilane, triethylsilane and hexamethyldislane. Useful alkoxysilanes are those with at least one silicon-hydrogen bond.

In a preferred embodiment, the molecular sieve catalyst is selectivated using the combined selectivation techniques of contacting the molecular sieve with a silicon compound and treatment with magnesium and/or phosphorus.

Usually the molecular sieve will be incorporated with a binder material resistant to the temperature and other conditions employed in the process. Examples of suitable binder material include clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The molecular sieve may also be composited with zeolitic material such as the zeolitic materials that are disclosed in U.S. Pat. No. 5,993,642. The relative proportions of molecular sieve and binder material will vary widely with the molecular sieve content ranging from between 1 to 99% by weight, more preferably in the range of 10 to 70% by weight of molecular sieve, and still more preferably from 20 to 50% by weight.

The methylation catalyst may also contain a hydrogenation metal, which may be present in the elemental state (i.e. zero valent) or in some other catalytically active form such as an oxide, sulfide, halide, carboxylate and the like. Preferably, the metal is used in its elemental state. Examples of suitable hydrogenation metals include Group VIIIA metals (i.e., Pt, Pd, Ir, Rh, Os, Ru, Ni, Co and Fe), Group IVB metals (i.e., Sn and Pb), Group VB metals (i.e., Sb and Bi), and Group VIIA metals (i.e., Mn, Tc and Re). Noble metals (i.e., Pt, Pd, Ir, Rh, Os and Ru) are sometimes preferred, most preferably Rh. The hydrogenation component may also be accompanied by another metal promoter.

Typically the hydrogenation metal is present on the catalyst in an amount from 0.1 wt. % to 5 wt. % of hydrogenation metal based on the weight of the catalyst. The incorporation of the hydrogenation metal can be accomplished with various techniques known to those skilled in the art. For example, the metal can be incorporated into the catalyst by impregnation, or by ion exchange of an aqueous solution containing the appropriate salt, or by a combination of these methods. By way of example, in an ion exchange process, platinum can be introduced by using cationic platinum complexes such as tetraammine-platinum (II) nitrate. In addition, the hydrogenation function can be present by physical intimate admixing, that is, the hydrogenation function can be physically mixed or extruded with the active catalyst. Physical intimate admixing can also be conducted by incorporating the hydrogenation function on a particle separate from the active catalyst, and then the particle carrying the hydrogenation function placed in close proximity to the catalyst. For example, the hydrogenation metal can be impregnated onto an amorphous support that is co-mingled with the active molecular sieve catalyst such as described in U.S. Pat. No. Re. 31,919 to Butter et al., incorporated by reference herein.

In one embodiment, the molecular sieve used in the methylation reaction has a hydrogenation metal comprising rhodium. The use of rhodium as the hydrogenation component has been found to reduce the amount of synthesis gas formed due to the decomposition of the alkylating agent (i.e. methanol in the preferred embodiment). In another embodiment, the molecular sieve used in accordance with this invention has a hydrogenation metal comprising platinum, and a selectivating compound comprising phosphorus. When such a molecular sieve is used in the process of this invention, and wherein water is co-fed into the reactor, the amount of synthesis gas formed due to the decomposition of the alkylating agent (i.e. methanol in the preferred embodiment) is found to be reduced.

Alkylation With Syngas

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reaction 5, and the following reverse water gas shift reaction:

$$CO_2 + H_2 \leftrightarrow CO + H_2O \quad \text{(reaction 6)}$$

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of 500° C. to 1200° C., such as 600° C. to 1000° C., for example 700° C. to 950° C. and a pressure of 1 kPa to 10,000 kPa, such as 2,000 kPa to 10,000 kPa, for example 3000 kPa to 5,000 kPa. Gas hourly space velocities may vary depending upon the type of process used, but generally the gas hourly space velocity of flow of gas through the catalyst bed is in the range of 50 hr$^{-1}$ to 50,000 hr$^{-1}$, such as 250 hr$^{-1}$ to 25,000 hr$^{-1}$, more preferably 500 hr$^{-1}$ to 10,000 hr$^{-1}$.

The effluent from the reverse shift reactor can then be fed to an alkylation reactor operating under conditions to cause reactions such as the following to occur:

$$CO + 2H_2 \leftrightarrow CH_3OH \quad \text{(Reaction 7)}$$

$$CH_3OH + C_6H_6 \rightarrow \text{toluene} + H_2O \quad \text{(Reaction 8)}$$

$$2CH_3OH + C_6H_6 \rightarrow \text{xylenes} + 2H_2O \quad \text{(Reaction 9)}$$

Thus the methylating agent includes CO, $CO_2$ and $H_2$ and/or $CH_3OH$ and derivatives thereof. The methylating agent reacts with benzene to form toluene, whereas toluene reacts with the methylating agent to form xylenes, preferably para-xylene. In one preferred embodiment of the invention, methanol as the methylating agent is not separately added but is formed in situ. The methylation process can be carried out as a batch type, semi-continuous or continuous operation utilizing a fixed, moving bed, or CSTR catalytic reaction system, with or without recycle. Multiple injection of the methylating agent may be employed. Suitable conditions for the methylation process include a temperature of 100 to 700° C., preferably 200 to 600° C., a pressure of 1 to 300 atmospheres (100 to 30,000 kPa), preferably 1 to 200 atmospheres (100 to 20,000 kPa), and a WHSV for the aromatic hydrocarbon of 0.01 to 100 hr$^{-1}$, preferably 1 to 50 h$^{-1}$. The composition of the feed, i.e. the mole ratio of $H_2/CO$ (and/or $CO_2$)/aromatic can be from of 0.01-10/0.01-10/0.01-10, preferably from 0.1-10/0.1-10/0.1-10.

A suitable catalyst for the methylation process comprises a molecular sieve typically together with one or metals or metal oxides, such as copper, chromium and/or zinc oxide. Typically, the alkylation catalyst contains from 5 wt. % metal or metal oxide first component/95 wt. % molecular sieve second component, to 95 wt. % metals or metal oxides first component/5 wt. % molecular sieve component. The molecular sieve can be any of aluminosilicate zeolites described above in relation to alkylation with methanol, such as ZSM-5, or can be an aluminophosphate material. Aluminophosphate-based materials usually have lower acidity compared to silicate-based materials. The lower acidity eliminates many side reactions, raises reactants' utilization, and extends catalyst life. In addition, some of the medium-pore aluminophosphate-based materials have unique channel structures that could generate the desirable shape selectivity.

Aluminophosphate-based materials are made of alternating $AlO_4$ and $PO_4$ tetrahedra. Members of this family have 8- (e.g. $AlPO_4$-12, -17, -21, -25, -34, -42, etc.), 10- (e.g. $AlPO_4$-11, 41, etc.), or 12- ($AlPO_4$-5, -31, etc.) membered oxygen ring channels. Although $AlPO_4$s are neutral, substitution of Al and/or P by cations with lower charge introduces a negative charge in the framework, which is countered by cations imparting acidity. Substitution of silicon for P and/or a P—Al pair turns the neutral binary composition (ie. Al, P) into a series of acidic-ternary-composition (Si, Al, P) based SAPO materials, such as SAPO-5, -11, -14, -17, -18, -20, -31, -34, -41, -46, etc. Acidic ternary compositions can also be created by substituting divalent metal ions for aluminum, generating the MeAPO materials. Me is a metal ion which can be selected from the group consisting of, but not limited to, Mg, Co, Fe, Zn and the like. Acidic materials such as MgAPO (magnesium substituted), CoAPO (cobalt substituted), FeAPO (iron substituted), MnAPO (manganese substituted), ZnAPO (zinc substituted) etc. belong to this category. Substitution can also create acidic quaternary-composition based materials such as the MeAPSO series, including FeAPSO (Fe, Al, P, and Si), MgAPSO (Mg, Al, P, Si), MnAPSO, CoAPSO, ZnAPSO (Zn, Al, P, Si), etc. Other substituted aluminophosphate-based materials include ElAPO and ElAPSO (where El=B, As, Be, Ga, Ge, Li, Ti, etc.). As mentioned above, these materials have the appropriate acidic strength for syngas/aromatic alkylation. The more preferred aluminophosphate-based materials of this invention include 10- and 12-membered ring materials (SAPO-11, -31, -41; MeAPO-11, -31, -41; MeAPSO-11, -31, 41; ElAPO-11, -31, -41; ElAPSO-11, -31, -41, etc.) which have significant shape selectivity due to their narrow channel structure.

As described above, where the alkylation catalyst includes a molecular sieve, the latter may be selectivated to change its diffusion characteristics such that the predominant xylene isomer produced by Reaction 9 is paraxylene. Suitable means of diffusion modification include steaming and ex-situ or in-situ deposition of silicon compounds, coke, MgO, and/or P on the surface or in the pore mouths of the molecular sieve, as described above. Alternatively, selectivation can be achieved by deposition of one or more organometallic compounds which are too bulky to enter the channels of the molecular sieve. One type of bulky organometallic compound suitable for para-alkyl selectivation is the salt of a large organic anion and a metallic cation. The organic anion can be selected from molecules containing carboxylic and/or phenolic functional groups, including but not limited to phthalate, ethylenediaminetetraacetic acid (EDTA), vitamin B-5, trihydroxy benzoic acid, pyrogallate, salicylate, sulfosalicylate, citrate, naphthalene dicarboxylate, anthradiolate, camphorate, and others. The metallic cations can be selected from the element(s) of Groups 1, 2, 3, 4, 5, 6, 7, 8, 9, 10, 11, 12, 13, 14, 15, and 16 of the Periodic Table of Elements (new IUPAC notation).

Para-alkyl selectivation with the above mentioned organometallic salts can be accomplished by various means. For example, a solution of an organometallic salt can be impregnated onto a silicate-based material or aluminophosphate-based materials. Either water or any suitable organic solvent can be used. Addition of non-metallic salts and/or adjustments of pH to facilitate the treatment are optional. Heat may be provided initially to drive off the solvent and leave behind a material coated homogeneously with an organometallic salt and to then convert the salt into a metal oxide. Alternatively, a dry-mix technique can be used, which involves mixing directly a zeolite in the form of powder or particles with a organometallic salt also in the form of powder or particles without the use of any solvent. The mixture will then be subjected to heat treatment, which facilitates the dispersion of the salt over the material and eventually turn the salt into metal oxide.

Also preferred is that an active metal be incorporated into the molecular sieve so as to saturate more highly reactive species, such as olefins, which may be generated as by-products and which could otherwise cause catalyst deactivation.

Prior to exposing the catalytic reaction systems to the feed components of toluene and/or benzene, $H_2$, CO, and/or $CO_2$ and/or methanol the catalytic reaction systems can optionally be activated under a reducing environment (e.g. 1-80% $H_2$ in $N_2$) at 150-500° C., and 1 to 200 atm (100 to 20,000 kPa) for 2 to 48 hours.

Toluene and/or benzene and the methylating agent(s) are usually premixed and fed together into the reaction vessel to maintain the desired ratio between them with no local concentration of either reactant to disrupt reaction kinetics. Optionally, instantaneous concentration of methylating agent can be kept low by staged additions thereof. By staged additions, the ratios of toluene and/or benzene to methylating agent concentrations can be maintained at optimum levels to give good aromatic compound conversions and better catalytic reaction system stability. Hydrogen gas and/or steam can also serve as an anticoking agent and diluent.

The method of this invention is capable of producing mixtures of xylenes where PX comprises at least 30 wt. % of the mixture, preferably at least 80 wt. %, and most preferably at least 90 wt. %. The method of this invention is also capable of converting at least 5 wt % of the aromatic compound to a mixture of xylenes, preferably greater than 15 wt. %.

Alkylated Product Recovery

Irrespective of the alkylation process employed, the effluent from the alkylation reaction system is fed to a separation section in which the aromatic products are initially separated from the hydrogen and other low molecular weight materials, conveniently by solvent extraction. The aromatics products can then be fractionated into a benzene fraction, a toluene fraction, a $C_8$ fraction and a heavy fraction containing naphthalene and alkylated naphthalenes. The $C_8$ aromatic fraction can then be fed to a crystallization or sorption process to separate the valuable p-xylene component and the remaining mixed xylenes either sold as product or fed to an isomerization loop to generate more p-xylene. The toluene fraction can either be removed as saleable product, recycled to the alkylation reactor or fed to a toluene disproportionation, preferably a selective disproportionation unit for the preparation of additional p-xylene.

Hydrogen Rejection

Hydrogen is a major component of the dehydrocyclization effluent. Accordingly, in an embodiment of this invention, after alkylation/recovery of the aromatic products, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species to produce water and a second effluent stream having a reduced hydrogen content compared with the first (dehydrocyclization) effluent stream.

Conveniently, the hydrogen rejection step may include (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins, and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2+$ enriched stream followed by methanation to achieve high conversion of the $H_2$.

Methanation/Ethanation

In one embodiment, the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \quad \text{(Reaction 10)}$$

$$2CO_2 + 7H_2 \leftrightarrow C_2H_6 + 4H_2O \quad \text{(Reaction 11)}$$

The carbon dioxide employed is conveniently part of a natural gas stream and preferably the same natural gas stream used as the feed to the dehydrocyclization step. Where the carbon dioxide is part of a methane-containing stream, the $CO_2:CH_4$ of the stream is conveniently maintained between 1:1 and 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2:CO_2$ molar ratio close to the stoichiometric proportions required for the desired Reaction 10 or Reaction 11, although small variations can be made in the stoichiometric ratio if it is desired to produce a $CO_2$-rich or $H_2$-rich second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a nicroporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of 100° C. to 900° C., such as 150° C. to 500° C., for example 200° C. to 400° C., a pressure of 200 kPa to 20,000 kPa, such as 500 to 5000 kPa and a weight hourly space velocity of 0.1 to 10,000 $hr^{-1}$, such as 1 to 1,000 $hr^{-1}$. $CO_2$ conversion levels are typically between 20 and 100% and preferably greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2:CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of 0.5:1 to 4:1, preferably 1.5:1 to 2.5:1, at a temperature of 175° C. to 400° C., preferably 180° C. to 240° C. and a pressure of 1 to 100 bar (100 to 10,000 kPa), preferably 10 to 40 bar (1,000 to 4,000 kPa), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnlium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, preferably cobalt, with rhenium or zirconium as a promoter, preferably cobalt and rhenium supported on silica or titania, preferably titania.

In another embodiment, the Fischer-Tropsch catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$—ZnO and ZSM-5 Catalysts for the Transformation of Syngas into Liquid Hydrocarbons* by Jose Erena; Ind. Eng. Chem Res. 1998, 37, 1211-1219, incorporated herein by reference.

The Fischer-Tropsch liquids, i.e., $C_5+$, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to the Fischer-Tropsch reaction whereby the carbon dioxide is converted to carbon monoxide by the reverse water gas shift reaction:

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO+CO_2$) in the range of from 0.5:1 to 20:1, preferably in the range of from 2:1 to 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from 150° C. to 450° C., such as from 175° C. to 350° C., for example from 200° C. to 300° C. Suitable pressures are in the range of from 1,500 kPa to 12,500 kPa, such as from 2,000 kPa to 10,000 kPa, for example 2,500 kPa to 7,500 kPa. Gas hourly space velocities vary depending upon the type of process that is used, but generally the gas hourly space velocity of flow of gas through the catalyst bed is in the range of from 50 $hr^{-1}$ to 50,000 $hr^{-1}$, such as from 250 $hr^{-1}$ to 25,000 $hr^{-1}$, more preferably from 500 $hr^{-1}$ to 10,000 $hr^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. patent application Ser. No. 10/671,281, filed Sep. 24, 2003 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of:

i) at least one metal from Group 3 and at least one metal from Groups 4-15 of the Periodic Table of the Elements;
ii) at least one metal from Groups 5-15 of the Periodic Table of the Elements, and at least one metal from at least one of Groups 1, 2, and 4 of the Periodic Table of the Elements;
iii) at least one metal from Groups 1-2, at least one metal from Group 3, and at least one metal from Groups 4-15 of the Periodic Table of the Elements; and
iv) two or more metals from Groups 4-15 of the Periodic Table of the Elements and (b) at least one of oxygen and sulfur, wherein the at least one of oxygen and sulfur is chemically bound both within and between the metals.

The selective hydrogen combustion reaction of the present invention is generally conducted at a temperature in the range of from 300° C. to 850° C. and a pressure in the range of from 1 atm to 20 atm (100 to 2000 kPa).

Aromatics Hydrogenation

In addition to the alkylation step, of the aromatic components in the dehydrocyclization effluent can be hydrogenated to generate useful products such as cyclohexane, cyclohexene, dihydronaphthalene(benzylcyclohexene), tetrahydronaphthalene(tetralin), hexahydronaphthalene(dicyclohexene), octahydronaphthalene and/or decahydronaphthalene(decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of 300 to 1,000° F. (150 to 540° C.), such as 500 to 700° F. (260 to 370° C.), a pressure of 50 to 2,000 psig (445 to 13890 kPa), such as 100 to 500 psig (790 to 3550 kPa) and a WHSV of 0.5 to 50 $hr^{-1}$, such as 2 to 10 $hr^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used.

An alternative hydrogenation process involves low pressure hydrocracling of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of 300 to 1,000° F. (150 to 540° C.), such as 500 to 700° F. (260 to 370° C.), a pressure of 50 to 2,000 psig (445 to 13890 kPa), such as 100 to 500 psig (790 to 3550 kPa) and a WHSV of 0.5 to 50 $hr^{-1}$, such as 2 to 10 $hr^{-1}$.

Referring now to the drawings, a first example of the invention is shown in FIG. 1, in which a natural gas feed 11 together with a recycle stream 12 from a reductive coupling reactor 13 is fed to a methanation reactor 14. In the methanation reactor 14, carbon dioxide in the feed 11 reacts with hydrogen in the recycle stream 12 to increase the methane concentration of the feed 11 and produce water as a by-product according to Reaction 10 above. The effluent stream 15 from the methanation reactor 14 is fed to a condenser 16, where water 17 is removed, and then the remaining effluent is fed to a furnace 18 where the temperature of the effluent is raised before being passed to the reductive coupling reactor 13. A side stream 19 from the recycle stream 12 is fed to furnace 18 to provide the fuel for the furnace.

In the reactor 13, the methane in the natural gas feed is dehydrocyclized to produce hydrogen and aromatic compounds, such as benzene and naphthalene, by Reactions 2 and 3 above as well as by-products such as ethylene and carbon monoxide as a result of Reactions 1, 4 and 5 above. Typically, a plurality of reactors 13 are connected in series with a furnace 18 being provided between successive reactors 13 to maintain the feed at the desired temperature as it undergoes the endothermic dehydrocyclization reaction in the reactors 13.

The effluent 21 from the reductive coupling reactor(s) 13 is fed to a solvent extraction tower 22 where the aromatic compounds are dissolved and removed as a bottoms stream 23, while the remainder of the effluent (comprising hydrogen, carbon monoxide, ethane, ethylene and unreacted methane) passes as overhead from the tower 22 as the recycle stream 12. The bottoms stream 23 is then passed to one or more fractionators 24 where the stream 23 is separated into a benzene-containing fraction 25, a naphthalene-containing fraction 26 and a solvent fraction 27. At least part of the benzene-containing fraction 25 and/or the naphthalene-containing fraction 26 is then fed to an alkylation reactor (not shown) and the solvent fraction 27 is recycled to tower 22.

In a modification (not shown) of the embodiment shown in FIG. 1, the effluent 21 from the reductive coupling reactor(s) 13 is cooled to condense out part of the aromatics component and then the remaining effluent is compressed before being fed to the extraction tower 22.

Figure 2:
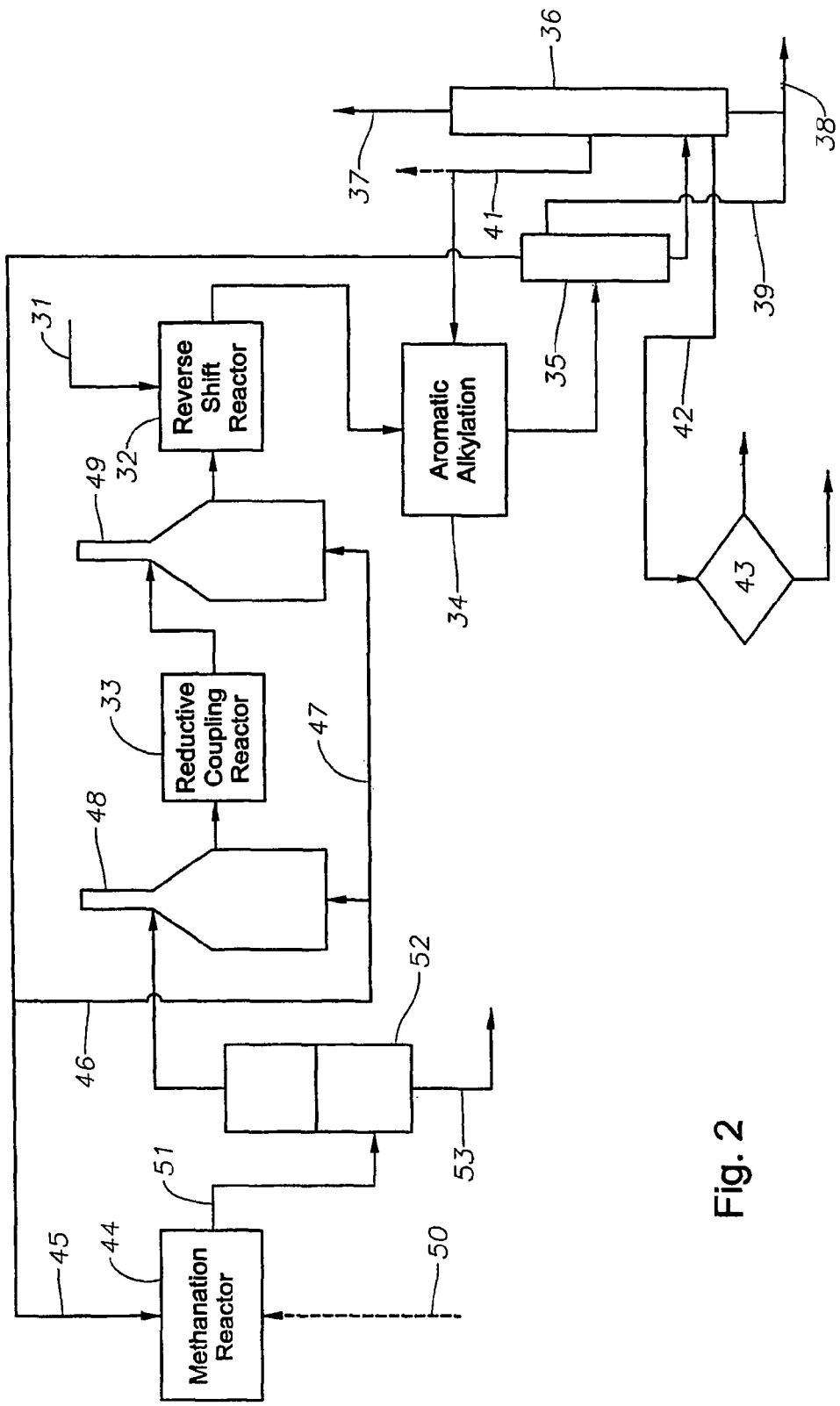
FIG. 2 is a flow diagram of a process for converting methane to aromatic hydrocarbons according to a second example of the invention.

Referring now to FIG. 2, in a process of a second example of the invention, a gas feed stream 31 containing $CO_2$ and possibly methane is fed to a reverse shift reactor 32 together with the hydrogen-rich, aromatics-containing effluent from a reductive coupling reactor 33. In the reductive coupling reactor 33, methane is dehydrocyclized to produce hydrogen and aromatic compounds, such as benzene and naphthalene, by Reactions 2 and 3 above as well as by-products such as ethylene and carbon monoxide as a result of Reactions 1, 4 and 5 above. Typically, a plurality of reactors 33 are connected in series with a furnace 48 being provided between successive reactors 33 to maintain the feed at the desired temperature as it undergoes the endothermic dehydrocyclization reaction in the reactors 33.

In the reverse shift reactor 32, carbon dioxide in the feed stream 31 reacts with methane, including unreacted methane in the effluent from the reductive coupling reactor 33, to produce carbon monoxide and hydrogen by reactions such as Reaction 5 above. The effluent from the reactor 32 is then fed to an alkylation reactor 34 where benzene and naphthalene produced in the reductive coupling reactor 33 are alkylated according to reactions such as Reactions 7 to 9 above.

The effluent from alkylation reactor 34 is fed to a solvent extraction tower 35 where the aromatic compounds are dissolved and passed to fractionator(s) 36 where they are separated into a benzene-containing fraction 37, a naphthalene-containing fraction 38, a solvent fraction 39, a toluene-containing fraction 41 and a $C_8$ fraction 42. The toluene-containing fraction 41 is either recycled to the alkylation reactor 34 or removed as product, while the $C_8$ fraction 42 is fed to a crystallizer 43 where the p-xylene isomer is removed from the remainder of the $C_8$ fraction by either crystallization or sorption technology. The solvent fraction 39 is recycled to the extraction tower 35.

The overhead from the extraction tower 35 (comprising hydrogen, carbon monoxide, ethane, ethylene and unreacted methane) is passed partly as a recycle stream 45 to a methanation reactor 44 and partly as slip streams 46, 47 to furnaces 48, 49 for providing heat to the reductive coupling reactor 33 and the reverse shift reactor 32, respectively. In the methanation reactor 44, carbon dioxide, carbon monoxide and hydrogen in the recycle stream 45 react to increase the methane concentration of the recycle stream and produce water as a by-product. An additional gas stream 50 containing $CO_2$ and possibly methane may also be fed to reactor 44 to accomplish greater conversion of the recycle hydrogen. It will be appreciated that at least one of the gas stream 31 and 50 contains methane and may be a natural gas stream.

The effluent 51 from the methanation reactor 44 is fed to a condenser 52, where water 53 is removed, and then the remaining effluent is fed to the furnace 48 where the temperature of the effluent is raised before being passed to the reductive coupling reactor 33.

Figure 3:
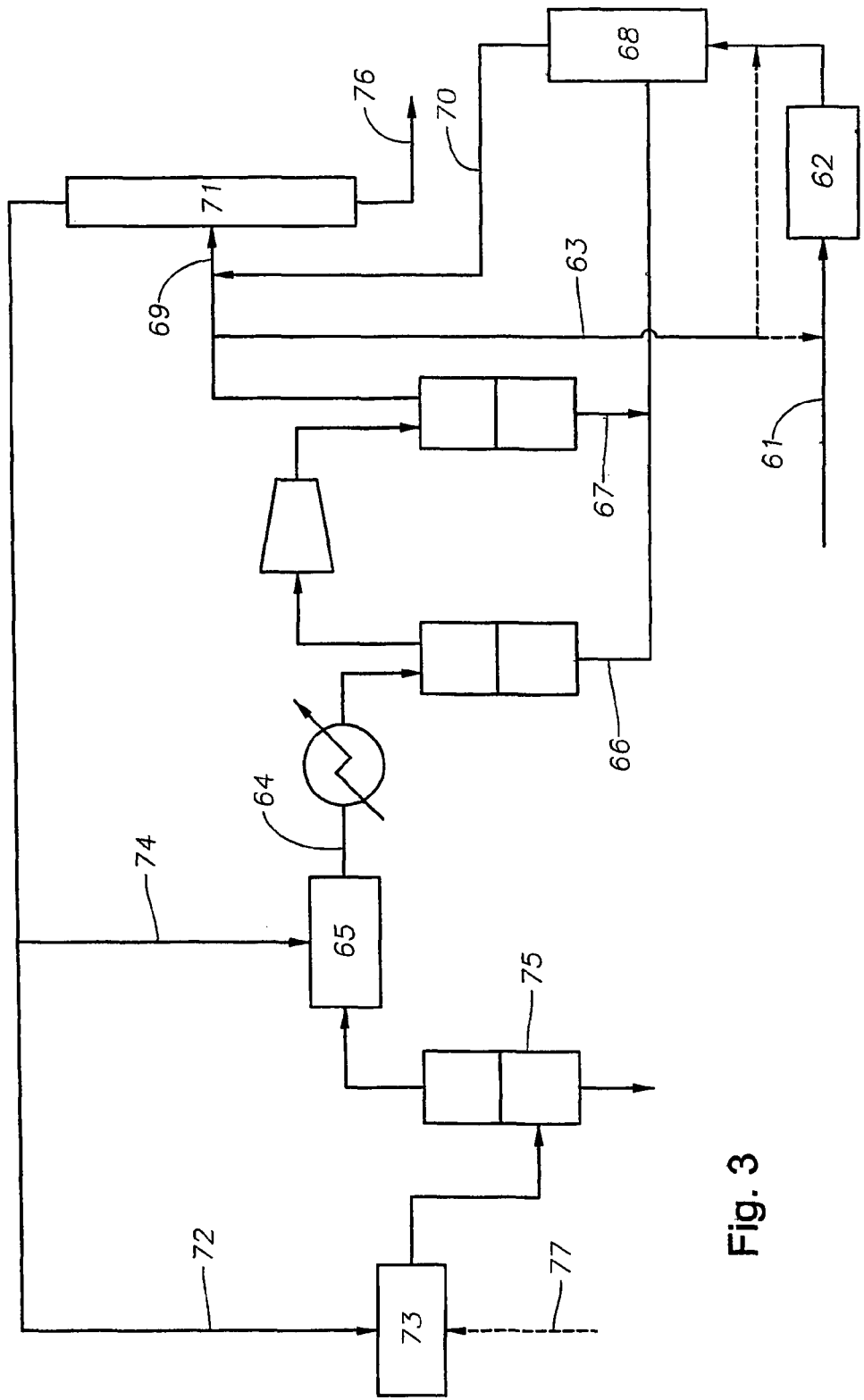
FIG. 3 is a flow diagram of a process for converting methane to aromatic hydrocarbons according to a third example of the invention.

Referring now to FIG. 3, in a process of a third example of the invention, a $CO_2$-containing natural gas stream 61 is fed to a reverse shift reactor 62 together with a hydrogen-rich, aromatics-depleted side stream 63 from the effluent 64 from a reductive coupling reactor 65. In this example, however, the effluent 64 from the reductive coupling reactor 65 is initially cooled to condense out a first benzene and naphthalene-containing stream 66 and is then comptessed to condense out a second benzene and naphthalene-containing stream 67 before removal of the side stream 63.

In the reverse shift reactor 62, carbon dioxide in the natural gas is reacted with methane to produce carbon monoxide and hydrogen by reactions such as, Reaction 5 above. The effluent from the reactor 62 and the first and second benzene and naphthalene-containing streams 66, 67 are then fed to an alkylation reactor 68 where benzene and naphthalene in the streams 66, 67 are alkylated according to reactions such as Reactions 7 to 9 above. If desired, part of the side stream 63 can be combined with the effluent from reactor 62 and/or the natural gas stream 61 to adjust the $H_2/CO/CO_2$ ratio of the feed to the alkylation reactor 68 and/or the reverse shift reactor 62.

The effluent 70 from the alkylation reactor 68 is the combined with the portion of the effluent 64 remaining after condensation of the streams 66, 67 and removal of the side stream 63 and the resulting combined stream 69 is fed to a solvent extraction tower 71. The aromatic compounds are dissolved out of the combined stream 69 in the tower 71 and are the passed as stream 76 to fractionator(s) (not shown) for separation into a benzene-containing fraction, a toluene-containing fraction, a $C_8$ fraction, a naphthalene-containing fraction and a solvent fraction. These fractions can then be handled in the same way as in the second example.

The overhead from the extraction tower 71 (comprising hydrogen, carbon monoxide, ethane, ethylene and unreacted methane) is passed partly as a recycle stream 72 to a methanation reactor 73 and partly as fuel stream 74 to a furnace (not shown) for supplying heat to the reductive coupling reactor 65. In the methanation reactor 73, carbon dioxide, carbon monoxide and hydrogen in the recycle stream 72 react to increase the methane concentration of the recycle stream and produce water as a by-product. An additional gas stream 77 containing $CO_2$ and possibly methane may also be fed to reactor 73 to accomplish greater conversion of the recycle hydrogen. The effluent from the methanation reactor 73 is fed to a condenser 74, where water is removed, and then the remaining effluent is fed to the reductive coupling reactor 65.

The invention will now be more particularly described with reference to the following Examples.

EXAMPLE 1

In a practical embodiment of the first example of the invention shown in FIG. 1, the feed 11 is a natural gas stream containing 30.5 wt % carbon dioxide. The reactor 14 contains a Cu/Zn catalyst and is operated at a temperature of about 300° C. and a pressure of 300 psia (2070 kPa). The reductive coupling reactor 13 contains a MoZSM-5 catalyst and is operated at a temperature of about 900° C. and a pressure of 50 kPa. The aromatic products separated by the fractionator(s) 24 comprise 90 wt % of benzene and 10 wt % of a naphthalene-containing heavy fraction.

100 kg of the benzene produced is combined with 92 kg of syngas (composed on 81 kg of CO, 11 kg of $H_2$) and fed to an alkylation reactor containing a supported $Cr_2O_3$/ZnO catalyst mixed with a silicon-selectivated PZSM-5 catalyst and operated at. a temperature of about 500° C. and a pressure of 400 psia (2760 kPa). The alkylation effluent is separated to remove a $C_8$ product stream comprising 136 kg of xylene having a para-concentration in excess of 90% and then the $C_8$-depleted effluent is separated into a benzene, toluene and (heavy $C_8$+) stream, which is recycled to the alkylation reactor and a lights stream comprising 45 kg water, 2 kg $CO_2$ and 9 kg of $C_5$−. The $C_5$− component can be separated from the lights stream and recycled to the reductive coupling reactor 13.

EXAMPLE 2

Example 1 is repeated but 100 kg of the benzene produced in the reductive coupling reactor 13 is combined with 106 kg of methanol and 1 kg of $H_2$ and fed to an alkylation reactor containing a silicon-selectivated PZSM-5 catalyst and operated at a temperature of about 501° C. and a pressure of 11 psig (177 kPa) and a WHSV of 3.9 $hr^{-1}$ and a hydrogen/hydrocarbon molar ratio of 1.8. The alkylation effluent is separated to remove a $C_8$ product stream comprising 136 kg of xylene having a para-concentration in excess of 90% and then the $C_8$-depleted effluent is separated into a benzene, toluene and (heavy $C_8$+) stream, which is recycled to the alkylation reactor and a lights stream comprising 58 kg water and 10.3 kg of $C_5$−. Again, the $C_5$− component can be separated from the lights stream and recycled to the reductive coupling reactor 13.

EXAMPLE 3

In a practical embodiment of the second example of the invention shown in FIG. 2, the feed 11 is a natural gas stream containing 25 wt % carbon dioxide and is fed only to the reverse shift reactor 32. The reactor 32 contains a Ni on titania catalyst and is operated at a temperature of about 900° C. and a pressure of 400 psia (2,760 kPa). The alkylation reactor 13 comprises a supported $Cr_2O_3$/ZnO catalyst mixed with a silicon-selectivated PZSM-5 catalyst and is operated at a temperature of about 500° C. and a pressure of 400 psia (2760 kPa). The aromatic products generated comprise 38 wt % of benzene and 10 wt % of a naphthalene, 48 wt % of p-xylene and 4 wt % of mixed xylenes.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for converting methane to alkylated aromatic hydrocarbons, the process comprising:
   (a) contacting a feed containing methane and at least one of $H_2$, $H_2O$, CO and $CO_2$ with a dehydrocyclization catalyst under non-oxidizing conditions effective to convert said methane to aromatic hydrocarbons and produce a first effluent stream comprising aromatic hydrocarbons and hydrogen;
   (b) contacting at least a portion of said aromatic hydrocarbon from said first effluent stream with an alkylating agent under conditions effective to alkylate said aromatic hydrocarbon and produce an alkylated aromatic hydrocarbon having more alkyl side chains than said aromatic hydrocarbon prior to the alkylating;
   (c) reacting at least part of the hydrogen from said first effluent stream with an oxygen-containing species comprising carbon dioxide or carbon monoxide to produce a second effluent stream having a reduced hydrogen content compared with said first effluent stream, wherein said second effluent comprises water and methane, ethane or a mixture of methane and ethane;
   (d) removing at least a portion of said water from said second effluent stream to produce a third effluent stream; and
   (e) recycling at least part of the methane and/or ethane from said second effluent stream to said contacting (a).

2. The process of claim 1, wherein said conditions in (a) include a temperature of about 400° C. to about 1200° C., a pressure about 1 kPa to about 1000 kPa and a weight hourly space velocity of about 0.01 to about 1000 $hr^{-1}$.

* * * * *